(12) United States Patent
Oldham et al.

(10) Patent No.: US 8,945,481 B1
(45) Date of Patent: Feb. 3, 2015

(54) MICROFLUIDIC DEVICES AND METHOD FOR THEIR USE

(75) Inventors: Mark F. Oldham, Los Gatos, CA (US); Kenneth J. Livak, San Jose, CA (US); Jason E. Babcoke, Suisun City, CA (US); H. Pin Kao, Fremont, CA (US); Stephen J. Gunstream, Redwood City, CA (US); Kevin S. Bodner, Belmont, CA (US); Douglas P. Greiner, Fremont, CA (US); Nigel P. Beard, Redwood City, CA (US); Dar Bahatt, Foster City, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 513 days.

(21) Appl. No.: 12/145,333

(22) Filed: Jun. 24, 2008

Related U.S. Application Data

(60) Provisional application No. 60/946,520, filed on Jun. 27, 2007.

(51) Int. Cl.
 *B01L 3/00* (2006.01)
(52) U.S. Cl.
 USPC .... 422/505; 435/6.12; 435/286.5; 435/287.2; 435/287.3; 435/288.2; 435/288.7

(58) Field of Classification Search
 USPC ............................................ 422/99, 102, 103
 See application file for complete search history.

(56) References Cited

U.S. PATENT DOCUMENTS

| 6,167,910 B1* | 1/2001 | Chow ............................ 137/827 |
| 6,438,279 B1* | 8/2002 | Craighead et al. ............... 385/12 |
| 2002/0092973 A1* | 7/2002 | Nagle et al. .................... 250/216 |
| 2004/0203136 A1* | 10/2004 | Kellogg et al. ............ 435/287.2 |
| 2004/0258885 A1* | 12/2004 | Kreutter et al. ............... 428/156 |
| 2005/0084421 A1* | 4/2005 | Unger et al. .................. 422/100 |
| 2005/0202468 A1* | 9/2005 | Koo et al. .......................... 435/6 |

* cited by examiner

*Primary Examiner* — Jill Warden
*Assistant Examiner* — Timothy G Kingan

(57) ABSTRACT

Exemplary embodiments provide microfludic devices and methods for their use. The microfluidic device can include an array of M×N reaction sites formed by intersecting a first and second plurality of fluid channels of a flow layer. The flow layer can have a matrix design and/or a blind channel design to analyze a large number of samples under a limited number of conditions. The microfluidic device can also include a control layer including a valve system for regulating solution flow through fluid channels. In addition, by aligning the control layer with the fluid channels, the detection of the microfluidic devices, e.g., optical signal collection, can be improved by piping lights to/from the reaction sites. In an exemplary embodiment, guard channels can be included in the microfluidic device for thermal cycling and/or reducing evaporation from the reaction sites.

11 Claims, 4 Drawing Sheets

MICROFLUIDIC DEVICES AND METHOD FOR THEIR USE

CROSS-REFERENCE TO RELATED APPLICATION

This application claims a priority benefit under 35 U.S.C. §119(e) from U.S. Patent Application No. 60/946,520 filed Jun. 27, 2007, which is incorporated herein by reference.

FIELD

This invention relates generally to microfluidic devices and, more particularly, to microfluidic devices and methods for their use in chemical and biological analysis and/or synthesis.

DESCRIPTION OF THE RELATED ART

Microfluidic devices with integrated fluidic circuits are known in the art. Examples of these are disclosed in U.S. Pat. Nos. 6,802,342; 6,951,632; 6,953,058; and U.S. Patent Publication Nos. 20060006067; 20050129581; and 20050119792, all of which are incorporated by reference herein in their entirety.

Conventional microfluidic devices with integrated fluidic circuits are formed of an elastomeric material and include a substrate and a plurality of fluid channels. The fluid channels form arrays of reaction sites to facilitate high throughput analyses. Alternatively, these devices can include a plurality of "blind channels" in which reaction sites are located at the end of a fluid channel. These devices promise reduced time, cost, and space requirements when used for a variety of microfluidic analyses and/or synthesis. It would therefore be desirable for improved microfluidic devices that can be used to conduct, for example, thermal cycling reactions.

BRIEF DESCRIPTION OF THE DRAWINGS

Various features of the embodiments can be more fully appreciated, as the same become better understood with reference to the following detailed description of the embodiments when considered in connection with the accompanying figures, in which.

DETAILED DESCRIPTION OF EMBODIMENTS

For simplicity and illustrative purposes, the principles of the present teachings are described by referring mainly to exemplary embodiments thereof. However, one of ordinary skill in the art would readily recognize that the same principles are equally applicable to, and can be implemented in, all types of microfluidic devices, and that any such variations do not depart from the true spirit and scope of the present teachings. Moreover, in the following detailed description, references are made to the accompanying figures, which illustrate specific embodiments. Electrical, mechanical, logical and structural changes may be made to the embodiments without departing from the spirit and scope of the present invention. The following detailed description is, therefore, not to be taken in a limiting sense and the scope of the present teachings is defined by the appended claims and their equivalents.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5.

According to various embodiments, the exemplary microfluidic devices can utilize a matrix design, a blind channel design, or a combination thereof. The matrix design can be used, for example, to analyze a large number of samples under a limited number of conditions. The matrix design microfluidic device can include a plurality of intersecting horizontal and vertical flow channels to define an array of reaction sites at the intersection of the horizontal and vertical flow channels. A valve system can enable solution to flow selectively through either the horizontal or vertical flow channels such that various flow channels in the matrix can be selectively isolated. Valves and pumps for regulating solution flow through flow channels of the device can be controlled, at least in part, by one or more control channels of a control layer that are separated from the flow channel by an elastomeric membrane or segment. In addition, by aligning the control layer with the flow channels, the detection of the reaction sites, e.g., optical signal collection, can be improved by piping the excitation/emission lights to/from the reaction sites.

Figure 1:
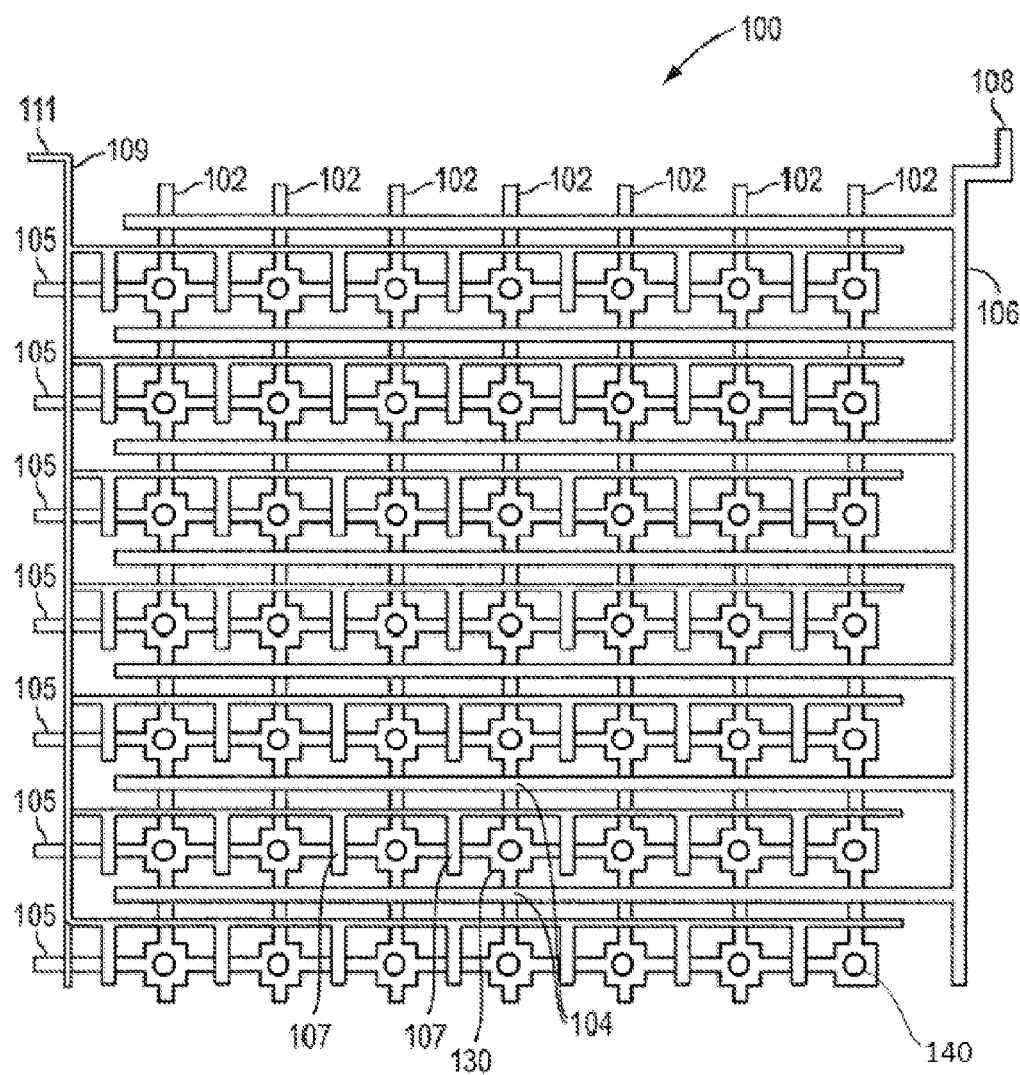
FIG. 1 is a schematic illustration of a microfluidic device in accordance with the present teachings.

A portion of an exemplary embodiment of a microfluidic device 100 using a matrix design is schematically shown in FIG. 1. Microfluidic device 100 can include a first plurality of fluid channels 105, wherein one of M different primers (e.g., DNA primers) can be introduced into each of the first plurality of fluid channels 105. Although only seven of M fluid channels 105 are shown in FIG. 1, one of ordinary skill in the art will understand that more than M and less than M fluid channels 102 are contemplated. The device can further include a second plurality of fluid channels 102, wherein one or more of N different samples can be introduced into each of the second plurality of fluid channels 102. Although only seven of N fluid channels 102 are shown in FIG. 1, one of ordinary skill in the art will understand that more than N and less than N fluid channels 105 are contemplated. The first plurality of fluid channels 105 and the second plurality of fluid channels 102 can intersect to form an array of M×N reaction sites 130. Microfluidic device 100 can further include a first plurality of valves 107 that control fluid flow within the first plurality of fluid channels 105 and a second plurality of valves 104 that control fluid flow within the second plurality of fluid channels 102. In an exemplary embodiment, microfluidic device 100 can include 49 fluid channels into which one of 49 different primers can be introduced. Exemplary microfluidic device 100 can further include an additional 49 fluid channels, into which 49 different samples can be introduced. The exemplary microfluidic device can then have 2401 reaction sites.

According to various other embodiments, the exemplary microfluidic devices can utilize a blind channel design that includes a plurality of blind channels. The blind channels can be flow channels having a dead end or isolated end such that solution can only enter and exit the blind channel at one end. Blind channel design microfluidic devices can be used to conduct a large number of analyses under different conditions with a limited number of samples. These devices differ from matrix design devices as they require only a single valve for each blind channel that forms a reaction site.

In matrix and blind channel microfluidic devices, flow of solution can be controlled, at least in part, by one or more control channels that are separated from the flow channel by an elastomeric membrane or segment. Referring back to FIG. 1, a first control channel 109 can control valves 107 to regulate flow in the first plurality of flow channels 105. First control channel 109 can be actuated by a first inlet 111. A second control channel 106 can control valves 104 to regulate flow in the second plurality of flow channels 102. Second control channel 106 can be actuated by a second inlet 108. The membrane or segment can be deflected into or retracted from the flow channels with which the control channel is associated by applying an actuation force to the control channels. By controlling the degree to which the membrane or segment is deflected into or retracted out from the flow channel, solution flow can be slowed or entirely blocked through the flow channel. Using combinations of control and flow channels, different types of valves and pumps can be formed for regulating solution flow.

Figure 3:
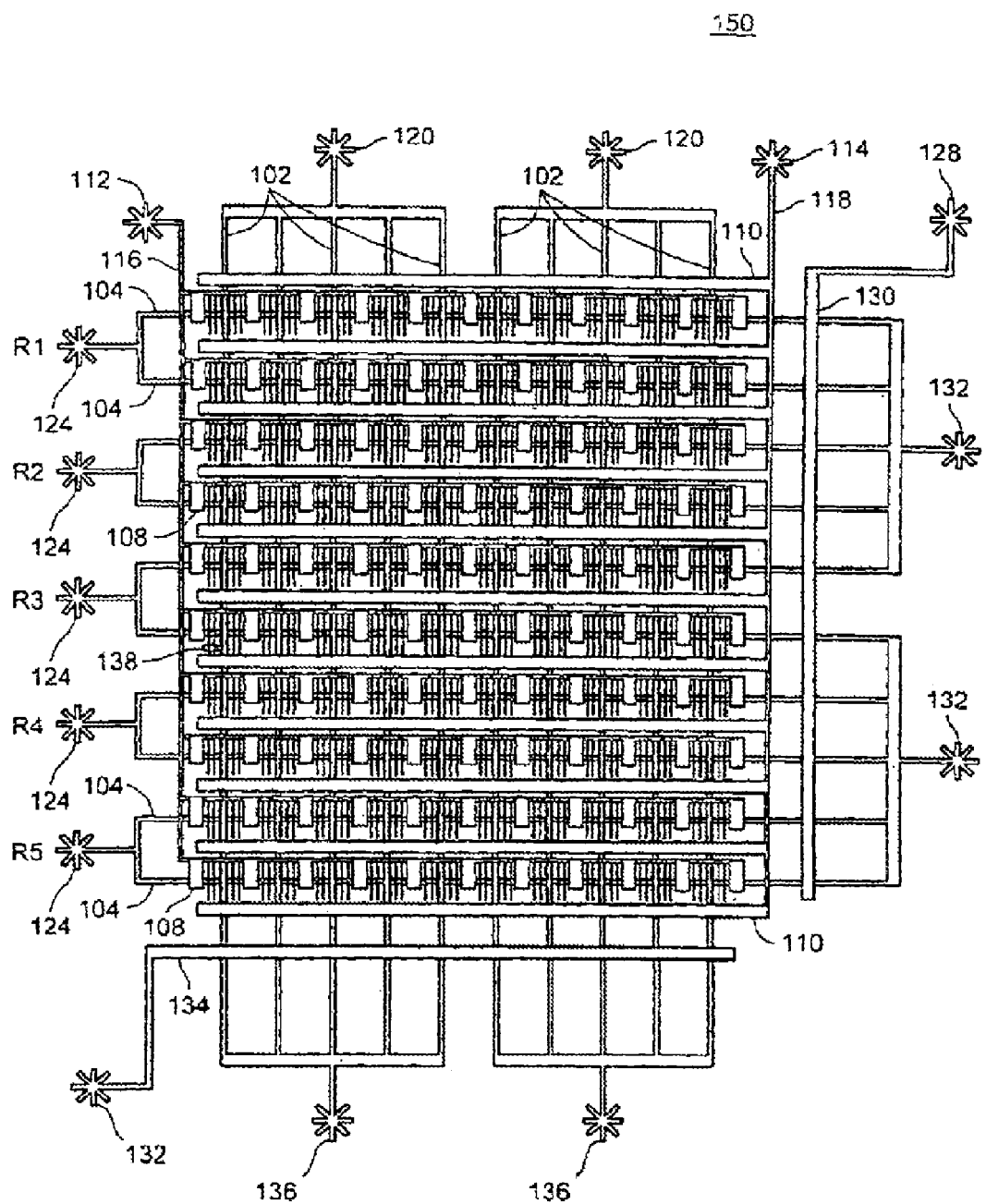
FIG. 3 shows a prior art microfluidics device.

In various embodiments, the exemplary microfluidic devices can further include guard channels in a guard layer to reduce evaporation of samples and reagents. For example, the guard channels may be configured as the guard channels 138 in FIG. 1F of US U.S. Patent Publication No. 20050129581, which is reproduced in FIG. 3 of the current application. The guard channels can be formed in a layer of elastomer that overlays the flow channels and/or reaction sites. In an exemplary embodiment, a light blocking dye can be included in the solution to reduce noise in optical detection. Similar to the control channels, the guard channels can be separated from the underlying flow channels and/or reaction sites by a membrane or segment of elastomeric material. Unlike control channels, however, the guard channels can be considerably smaller in cross-sectional area.

Figure 4:
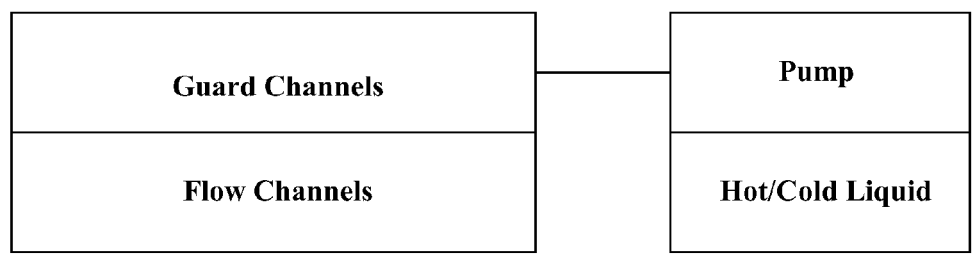
FIG. 4 is a schematic representation of a microfluidics device according to an embodiment of the present invention.

Referring to FIG. 4, the guard channels can be designed to be pressurized to allow a solution, such as water, to flow into the guard channel. For example, the guard channels can be used to perform thermal cycling for the flow channels and/or reaction sites. In an exemplary embodiment, the thermal cycling can be performed using the guard channels by pumping a hot or cold liquid, such as water or ethylene glycol. In various embodiments, the guard channels can be configured, for example, overlay and/or underlie the flow channels and/or reaction sites.

Exemplary microfluidic devices can be formed of elastomeric materials by, for example, single and/or multilayer soft lithography (MSL) techniques and/or sacrificial-layer encapsulation methods. In various embodiments, the fluid (flow) channels can be formed of an elastomer and/or a coating disposed on the elastomer, where the coating includes silicon. In various other embodiments, the fluid channels can further include a coating to avoid degradation of, for example, reference dye 6-carboxy-X-rhodamine (ROX). To achieve a desired optical or thermal property, the fluid channels can be formed of, for example, polydimethylsiloxane (PDMS) doped with, for example, carbon, $TiO_2$ and/or $ZnO_2$.

Operation of an exemplary microfluidic device will now be discussed with reference back to FIG. 1 and microfluidic device 100 including 49 first fluid channels and 49 second fluid channels. One of 49 primers can be introduced into respective ones of the 49 first fluid channels 105. The primers can mix with the samples at each of the 2401 reaction sites 130. In various embodiments, microfluidic device can be coupled to a themocycler in order to undergo thermal cycling, for example, using the guard channels.

According to various other embodiments, one or more reagents can be deposited at the reaction sites 130 during fabrication of the exemplary microfluidic devices. This can result in a reduction in the number of input and outputs. For example, in an embodiment, a bead 140 can be provided in each of the reaction sites. The bead 140 can be preloaded with a primer, e.g., a DNA primer. After a desired reaction using the primer, the flow channels and valve system can be used to wash the reaction site prior to a next desired reaction.

Reaction sites (e.g., 130 in FIG. 1) can be monitored using a variety of detection systems including, for example, optical detection systems. Because the exemplary microfluidic devices can be made of elastomeric materials that are relatively optically transparent, optical detection can occur at the reaction site itself (e.g., at the intersection of flow channels in a matrix design or at the blind end of a flow channel). Detection can be accomplished using detectors that are incorporated into the device or that are separate from the device but aligned with the reaction sites, for example, using detectors 201 shown in FIG. 2. In various embodiments, the reaction sites can include a molded lens to aid optical detection. The molded lens can be formed of, e.g., one or more of a glass, a cyclo-olefin polymer (COP), a cyclo-olefin copolymer (COC), a plastic, and a polycarbonate. In various embodiments, fluorescence polarizing anisotropy measurement can be made using a polarizing filter.

Figure 2:
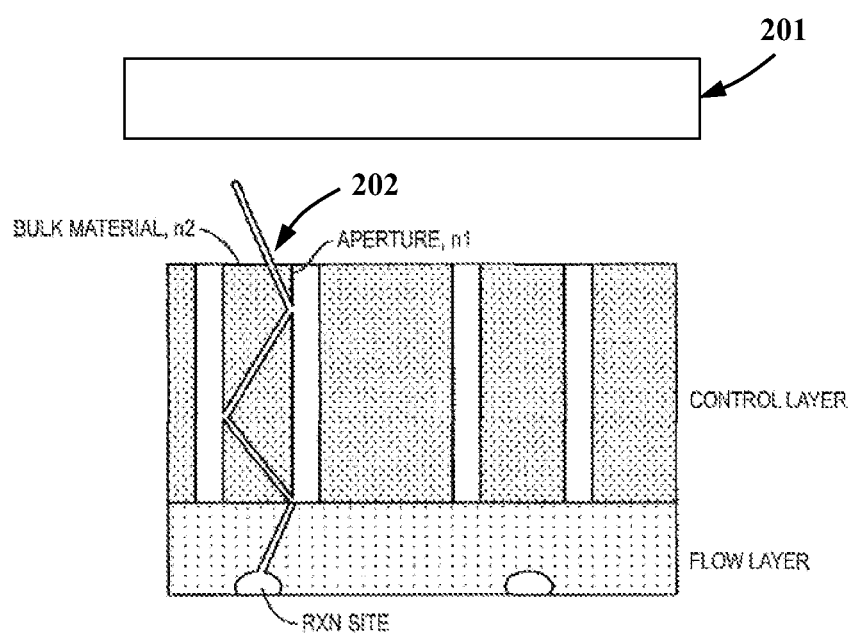
FIG. 2 shows an exemplary system for collecting optical signal from reaction sites in microfluidic channels in accordance with the present teachings.

For example, FIG. 2 shows an exemplary system for collecting optical signals from the reaction sites of the microfluidic channels in accordance with the present teachings. As shown, a control layer can be overlaid on top of a flow layer. The flow layer can include various flow channels intersecting various reaction sites, for example, one or more of the M×N reaction sites 130 in FIG. 1. The control layer can include a plurality of apertures having a medium, such as air or water, with a refractive index of n2, formed in a bulk material (e.g., the transparent material such as PDMS used for the control layer as described above) having a refractive index of n2. The refractive index n2 of the bulk material is generally greater than n1 of the medium in the closest neighboring apertures. In an exemplary embodiment, the control layer can be formed over the flow layer having reaction sites aligned underneath the bulk material of the control layer. During optical detection, for example using the plurality of optical detectors 201, a total internal reflection can occur along an optical path 202 to confine ("pipe") light in the area of the bulk material and the aligned respective reaction sites, defined by the closest neighboring apertures. The collection efficiency can increase due to the light confinement. In various embodiments, guard layers having the guard channels can be configured to overlay and/or underlie the microfluidic system shown in FIG. 2. For example, the guard layer can be configured under the flow layer for a thermal cycling.

While the invention has been described with reference to the exemplary embodiments thereof, those skilled in the art will be able to make various modifications to the described embodiments without departing from the true spirit and scope. The terms and descriptions used herein are set forth by way of illustration only and are not meant as limitations. In particular, although the method has been described by examples, the steps of the method may be performed in a different order than illustrated or simultaneously. Those skilled in the art will recognize that these and other variations are possible within the spirit and scope as defined in the following claims and their equivalents.

What is claimed is:

1. A microfluidic device comprising:
   a first plurality of fluid channels, wherein one of M different primers can be introduced into each of the first plurality of fluid channels;
   a second plurality of fluid channels, wherein one or more of N different samples can be introduced into each of the second plurality of fluid channels;
   a plurality of valves that control fluid flow within the first and the second plurality of fluid channels, wherein at least some of the first plurality of fluid channels and the second plurality of fluid channels intersect to form an array reaction sites; and
   a thermal cycler comprising:
      a plurality of guard channels disposed over or under the reaction sites;
      a source comprising a hot liquid and a cold liquid that is colder than the hot liquid; and
      a pump configured to perform thermal cycling by alternately flowing the hot liquid and the cold liquid into the guard channels.

2. The microfluidic device of claim 1, wherein the fluid channels comprise an elastomer and a coating comprising silicon disposed on the elastomer.

3. The microfluidic device of claim 2, wherein the fluid channels comprise polydimethylsiloxane (PDMS) doped with carbon to achieve a desired optical or thermal property.

4. The microfluidic device of claim 2, wherein the fluid channels comprise polydimethylsiloxane (PDMS) doped with one or more of $TiO_2$ and $ZnO_2$ to achieve a desired thermal property.

5. The microfluidic device of claim 1, further comprising a bead located in each of the reaction sites.

6. The microfluidic device of claim 1, wherein one or more of the reaction sites further comprise a molded lens.

7. The microfluidic device of claim 6, wherein the molded lens comprises one or more of a glass, a cyclo-olefin polymer (COP), a cyclo-olefin copolymer (COC), a plastic, and a polycarbonate.

8. The microfluidic device of claim 1, further comprising an optical detection system comprising a light pipe.

9. The microfluidic device of claim 1, wherein the guard channels are disposed over the at least some of the reactions sites.

10. The microfluidic device of claim 1, wherein the fluid channels are configured to wash at least some of the reaction sites prior to a subsequent reaction.

11. The microfluidic device of claim 5, wherein the bead is preloaded with a primer.

* * * * *